United States Patent [19]

Martin et al.

[11] Patent Number: 4,842,825

[45] Date of Patent: * Jun. 27, 1989

[54] APPARATUS FOR DETERMINING CHEMICAL STRUCTURE

[75] Inventors: Stephen J. Martin, Katy; Raymond D. Worden, Houston, both of Tex.

[73] Assignee: Ruska Laboratories, Inc., Houston, Tex.

[*] Notice: The portion of the term of this patent subsequent to Nov. 15, 2005 has been disclaimed.

[21] Appl. No.: 876,129

[22] Filed: Jun. 19, 1986

[51] Int. Cl.$^4$ .................. G01N 25/22; G01N 31/12
[52] U.S. Cl. .................................. 422/80; 422/93; 422/98; 422/89; 436/157; 436/158; 436/159; 436/160; 73/863.58
[58] Field of Search .............. 422/80, 93, 98, 89; 436/157, 158, 159, 160; 73/863.51, 863.58

[56] References Cited

U.S. PATENT DOCUMENTS

| | | | |
|---|---|---|---|
| 3,475,131 | 10/1969 | Keulemans | 422/80 |
| 3,798,973 | 3/1974 | Estey | 73/863.58 X |
| 3,921,458 | 11/1975 | Logan | 73/863.58 X |
| 4,244,917 | 1/1981 | Woods et al. | 422/80 X |

Primary Examiner—Barry S. Richman
Assistant Examiner—Lynn M. Kummert
Attorney, Agent, or Firm—Browning, Bushman, Zamecki & Anderson

[57] ABSTRACT

An assembly of nonreactive material receives a sample of material to be analyzed which is then placed in an environmentally controlled pyrolysis chamber. As the sample is selectively heated, an inert carrier gas is admitted to the chamber to wash the gases from the sample through trap and splitter assemblies where a portion of the sample gas is tapped off by a capillary column. The temperature of the gas in the capillary column is controlled as known makeup gases are added prior to passing through a detector, such as a flame ionization detector, to determine the components of the sample gas. The capillary tube can also be coated with an apolar liquid phase separation material.

11 Claims, 3 Drawing Sheets

APPARATUS FOR DETERMINING CHEMICAL STRUCTURE

BACKGROUND OF THE INVENTION

1. Field of the Invention

The present invention relates to an improved apparatus useful in identifying the chemical nature or structure of substances, and, more particularly, an improved apparatus for pyrolyzing substances to generate volatile and breakdown components of such substances.

2. Description of the Prior Art

Numerous analytical techniques such as gas chromotography, mass spectroscopy, infared spectroscopy, etc. are available for analyzing chemical compounds and mixtures. However, many, complex chemical substances, particularly solids, cannot be analyzed effectively by such techniques because of the myriad of individual chemical compounds present in the substances or because the substance is a highly complex material, e.g. a polymer.

One area where analysis of complex chemical substances is extremely important involves petroleum exploration. It is common, during drilling an oil or gas well, to regularly chemically analyze formation samples taken from the well to determine the presence of commercial quantities of hydrocarbon material. Typically, such analyses have been carried out through laborious and time consuming chemical techniques which must be carried out in a well equipped laboratory precluding effective and rapid on-site analysis of the samples. Considering that the hydrocarbon content of source rock and reservoir rock formations is extremely critical in determining whether to continue drilling, or to institute production procedures from the well, rapid, on-site analysis of the source rock or reservoir rock is clearly desirable.

There are other instances in which the chemical makeup of a substance is difficult to ascertain with conventional analytial techniques. For example, in the case of polymeric materials, precise chemical structure is often times impossible to ascertain. Naturally occurring chemical substances, such as materials derived from plant sources, also present extremely complex mixtures of chemical compounds which are difficult to analyze using conventional techniques.

In all of the instances mentioned above, analysis would be greatly facilitated if the complex chemical substances could be "taken apart", either by evolving the more volatile components from the substances and/or by breaking down the non-volatile components into compounds which are more easily identified. To this end, pyrolytic analysis has proved to be a valuable tool in the analysis of complex chemical substances.

As is well known, in a typical pyrolysis technique, the substance to be analyzed is subjected to increasing temperature so as to accomplish a selective release of the volatile components from the substance generally followed by applying a temperature at which the non-volatile components are degraded or pyrolyzed into breakdown products which are more susceptible to analysis.

Unfortunately, the pyrolysis technique suffers from several disadvantages. For one, because the volatile components or breakdown components from the substance being analyzed are at elevated temperature, they are prone to reaction to form other products which will give misleading results as to the composition of the original substance. Since many apparatuses used for pyrolysis employ reactive materials, such as stainless steel and other metals, the volatile products and/or breakdown products can react or be adsorbed on these "chemically active" surfaces and either be converted into other products, react with other volatile or breakdown components to form new products or be held by the adsorbent surfaces and not reach the detector.

SUMMARY OF THE INVENTION

The present invention is capable of overcoming many of the above discussed problems of the prior art by providing an improved pyrolysis apparatus for making accurate and repeatable determinations of the chemical content of samples. These determinations can be made rapidly and on site, as opposed to under laboratory conditions, while minimizing unwanted side reactions from components or breakdown products released from the sample being analyzed.

The subject improved pyrolysis apparatus has a sample receiving assembly formed almost entirely of fused quartz and including means to feed carrier gas to wash over the sample. A temperature controlled pyrolysis chamber, also of fused quartz, receives the sample assembly therein, and gases generated from pyrolysis of the sample material are carried from the pyrolysis chamber successively to trap and splitter assemblies which separate a determined portion of the sample gas and carrier gas for subsequent testing after combination with a known makeup gas prior to the final flame ionization detection. The portions of the subject pyrolysis apparatus defining the sample gas path are formed of quartz so as to not react with or adsorb the gases. The apparatus has heating and cooling means spaced along its height to provide accurate temperature control for accuracy and repeatability of the testing. The major portion of the sample and carrier gas mixture purged from the apparatus can be recovered for subsequent comparison or repeated testing.

BRIEF DESCRIPTION OF THE DRAWINGS

The present invention will now be described, by way of example, with reference to the accompanying drawings in which FIGS. 1A, 1B and 1C together form a continuous longitudinal section through the present invention from bottom to top.

DETAILED DESCRIPTION OF THE PRESENT INVENTION

Figure 1A:
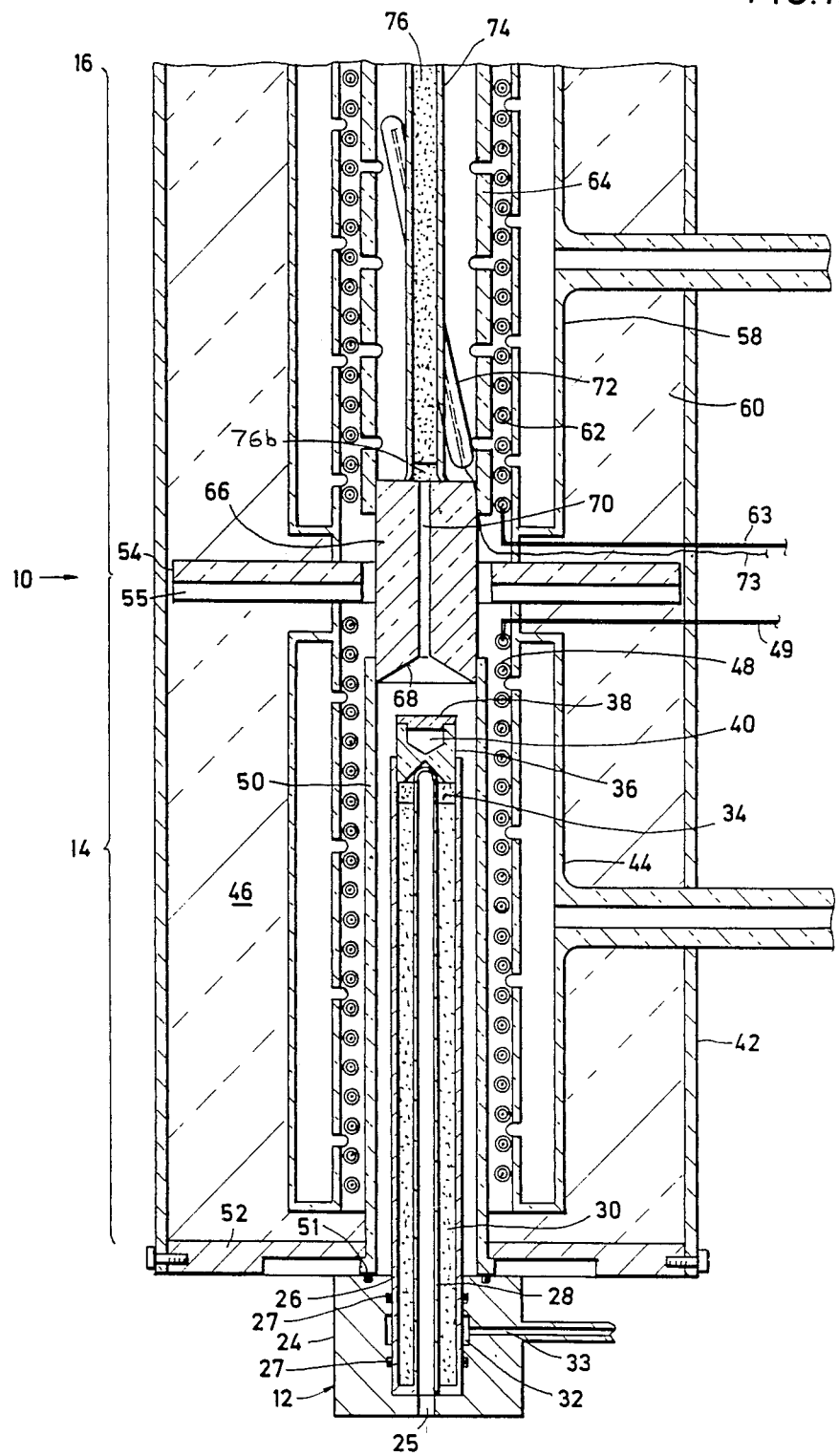
Figure 1B:
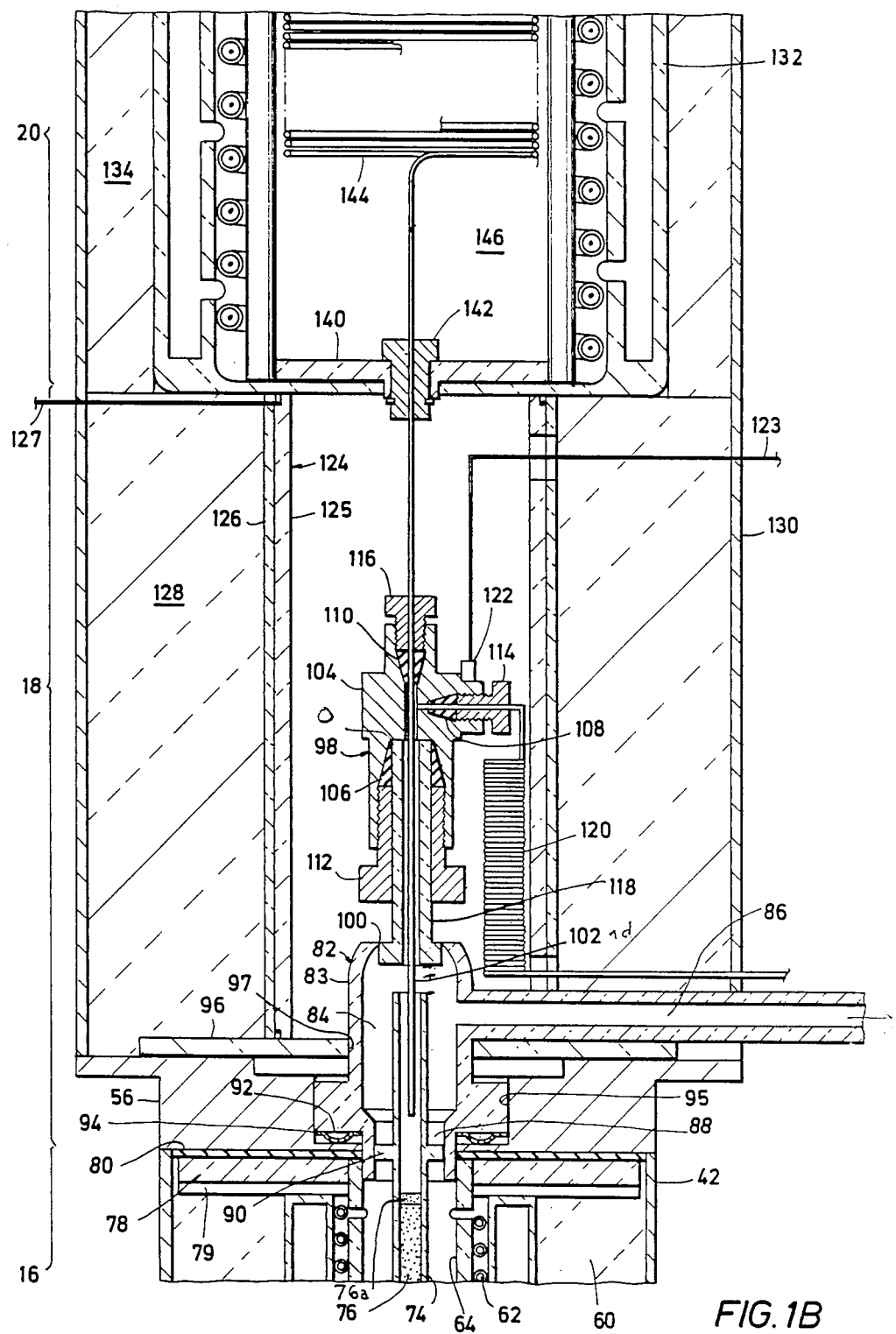
Figure 1C:
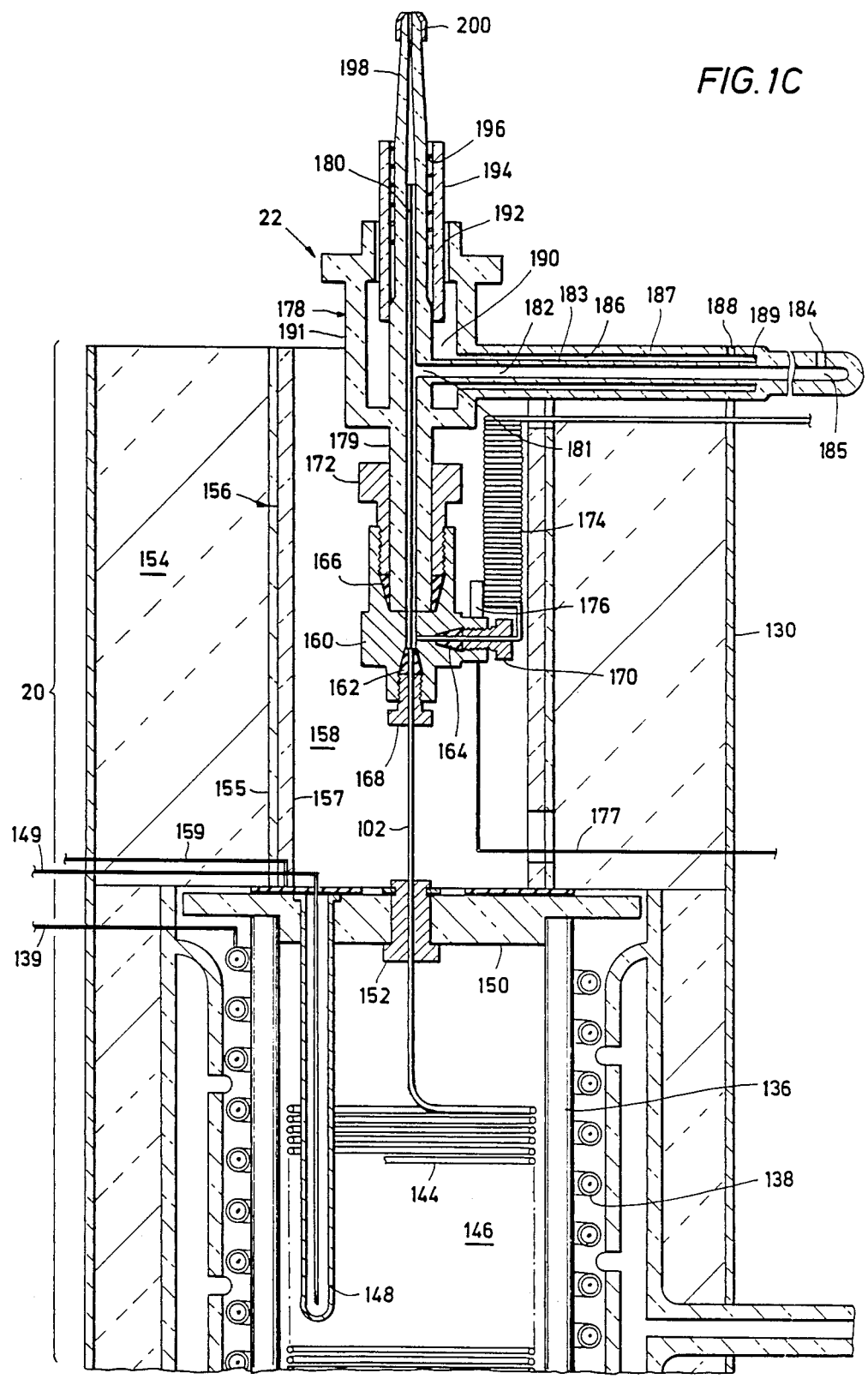

The subject invention is a continuous elongated member and has been shown in three sections in the figures for convenience in illustrating the various portions thereof with adequate size. Since the subject invention is a vertical unit, FIGS. 1A–1C represent the invention from the bottom to the top.

The subject pyrolysis apparatus 10 has, from bottom to top, a sample tube assembly 12, which is received in a sample chamber portion 14 forming the base of the apparatus, trap portion 16, splitter portion 18, and column portion 20 which receives a flame ionization detector assembly 22 at its upper end.

The sample tube assembly 12 has a metal base 24 which supports a tubular fused quartz member 26 therein. A quartz resistance temperature detector receiving tube 28 is mounted concentrically within the member 26 and the annular space therebetween is filled with quartz 30 in wool or granular form. Tube 28 opens through a bore 25 in base 24 to receive a temperature probe (not shown) therein. A chamber 32 in base 24 surrounds and communicates with the lower end of the tubular member 26 through ports (not shown). The chamber 32 is sealed by O-rings 27 and is fed through port 33 which, in turn, is connected to a source (not shown) of carrier gas, such as helium. An annular quartz member 34 supports the upper end of tube 28 within the tubular member 26. A quartz sample bucket or boat 36 is received on the upper end of the tubular member 26 engaging the resistance temperature detector receiving tube 28. A removable quartz cover 38 closes the bucket 36 to define a sample chamber 40 therebetween. The annular member 34, bucket 36 and lid 28 are all formed of gas permeable quartz.

The sample chamber portion 14 of the subject pyrolyzer includes a cylindrical outer shell 42, which may be made of metal for strength, having a first quartz cooling chamber 44 concentrically mounted therein. The annulus between the outer shell 42 and the cooling chamber 44 is filled by thermal insulation 46. A first heater 48 is mounted coaxially within the cooling chamber 44 and receives a tubular quartz body 50 therein. The first heater 48 is shown as an electrical resistance heater wound around tubular body 50 and connected to a source of power (not shown) through leads 49. The tubular quartz body 50 has an annular seal 51 on the bottom end to engage base 24 of the sample tube assembly 12, the upper end being an open outlet. This portion of the invention is completed at the lower end by a base 52 secured to both the shell 42 and the tubular body 50 and at the upper end by a vented spacer 54. The vented spacer 54 is an annular quartz member having a plurality of radially directed grooves 55 on the lower side thereof.

The trap portion 16 is in the upper portion of outer shell 42 between the vented spacer 54 and a pyro mounting plate 56. A second quartz cooling chamber 58 is mounted in this area concentrically within the outer shell 42 with thermal insulation 60 filling the annulus therebetween. A second heater 62 is mounted concentrically within the second quartz cooling chamber 58 and a quartz trap tube 64 is mounted concentrically inside the second heater 62. The second heater 62 is also shown as an electrical resistance heater wound around trap tube 64 and connected by leads 63 to a power source (not shown). The trap tube 64 is connected to the tubular body 50 of the sample chamber portion 14 by means of a quartz cylindrical interconnect body 66 having a profiled, downwardly directed entry 68 and an axial passage 70. Tubular body 50, interconnect body 66 and trap tube 64 are preferably fused together to form a continuous gas passage. A resistance temperature detector 72 is positioned within the trap 64 and tangentially engages an axially extending fused quartz trap tube 74 which is substantially filled with quartz sand 76 and retained therein by quartz wool plugs 76a and 76b. The resistance temperature detector 72 is connected by leads 73 to a power source (not shown). A second vented spacer 78 is mounted at the upper end of the trap portion 16 separated from mounting plate 56 by an insulated washer 80. The second vented spacer 78 is also an annular quartz member having a plurality of radially directed grooves 79 on the lower side thereof.

The splitter portion 18 is formed by a fused quartz splitter assembly 82 which has body 83 defining an axially extending chamber 84 with an integral vent tube 86 extending radially from the chamber 84. The upper end of the trap tube 74, with integral flange 90, is coaxially mounted within lower end 88 of body 83. The splitter assembly 82 has an integral outwardly directed annular flange 92, one side of which engages an annular spring washer 94 in recess 95 in mounting plate 56. The splitter assembly 82 is also received in the central aperture 97 of an annular quartz mounting disk 96. A lower T-assembly 98 is attached to a quartz capillary tube 118 which is fused to splitter assembly 82 at 100. The lower end of capillary column 102 is mounted in lower T-assembly 98 by means of seal 110 in such manner as to provide coaxial alignment with the bore of capillary tube 118 and trap tube 74 and further provides vertical locating means for positioning the end of capillary tube part way into the trap tube just above the quartz wool trap packing plug 76a. The lower T-assembly 98 includes a T-shaped stainless steel body 104 with ferrules 106, 108, 110 and stainless steel nuts 112, 114, 116 received in the respective passages thereof. Ferrule 106 and nut 112 hold the assembly 98 in place on capillary tube 118. Ferrule 108 and nut 114 hold the upper end of a purge gas heater coil 120. The coil 120 is connected to a source (not shown) of purge gas, such as helium, to facilitate sweeping of the bore of capillary tube 118 and chamber 84. Nut 116 and ferrule 110 secure the capillary tube 102 in place. A resistance temperature detector 122 is mounted adjacent the heater coil 120 to monitor its input to the T-body 104. The detector 122 is connected by leads 123 to a resistance measuring device (not shown). The entire splitter portion is enclosed within an annular third heater assembly 124, formed by a pair of concentric fused quartz sleeves 125, 126 enclosing a heater coil (not shown) connected by leads 127 to a source of power (not shown). Annular thermal insulation 128 and annular outer shell 130 enclose the heater assembly 124 and complete the splitter portion 18.

The column portion 20 of the subject pyrolyzer has a third quartz cooling chamber 132 mounted concentrically within the shell 130 with the annulus therebetween filled by thermal insulation 134. A quartz cage assembly 136 is mounted spaced concentrically within the third cooling chamber 132 with a fourth heater 138 filling the annulus therebetween. The fourth heater 138 is a further electrical resistance heater wound around cage 136 and connected by leads 139 to a resistance detector (not shown). An annular fused quartz plate 140 forms the base of the cage assembly 136 and receives therein a bored fused quartz plug 142 through which the capillary column 102 passes. The capillary tube 102 forms a helix 144 within the chamber 146 defined by the cage assembly 136. The cage assembly 136 can be a slotted cylinder or an annular arrangement of bars, for example. At least the helical coil portion of the capillary tube is coated with an apolar liquid phase material. A resistance temperature detector 148 extends into the chamber 146 in close proximity to the helix 144 and is connected to a resistance detector (not shown) by leads 149. The top of the chamber 146 is closed by a quartz lid 150 having a bored plug 152 through whch the capillary column 102 passes to the flame ionization detector assembly 22.

The upper end of the column portion includes, working inwardly from the outer shell 130, annular thermal insulation 154, and annular fifth heater assembly 156 defining a central chamber 158. The fifth heater assembly 156 is formed by a pair of concentric fused quartz sleeves 155, 157 enclosing a heater coil (not shown) connected to a power source (not shown) by leads 159.

A stainless steel upper T-assembly 160 is mounted within the chamber 158 with ferrules 162, 164, 166 and nuts 168, 170, 172 received in the respective passages thereof. The ferrule 162 and nut 168 secure the upper end of the capillary column 102. The ferrule 164 and nut 170 secure one end of a makeup gas heater coil 174, the other end of which is connected to a source (not shown) of makeup gas, such as nitrogen. A resistance temperature detector 176 is mounted closely adjacent this connection to monitor the temperature thereof and connected by leads 177 to a resistance detector (not shown). The ferrule 166 and nut 172 secure the upper assembly 160 to the lower end of the quartz flame ionization detector 22.

The flame ionization detector 22 has a fused quartz body 178 with a depending quartz capillary tube 179 defining an axial mixing chamber and passage 180 intersected by a radially directed port 181 having a tube 183 forming first passage 182 opening on a bore 185 having a port 184 at its outer free end, the port being connected to a source of hydrogen (not shown). Tubular arm 187 forms an annular chamber 186 about tube 183 with a port 188 connecting the chamber 186 to a source of air (also not shown) by means of annular chamber 186. Tubular arm 187 forms a shoulder 189 against which one end of tube 183 is fused, the other end being fused to body 178. Chamber 186 opens onto chamber 190 which is defined by quartz body 191 and is coaxial with passage 180. Chamber 190 has an annular exit port 192 receiving concentrically therein a cylindrical quartz shield 194, heater coil 196 and the nozzle-like upper end 198 of the quartz body 178. The upper end of mixing chamber and passage 180 and the bore of nozzle end 198 are both larger than the bore of capillary column 102 to prevent back flow of gases. An electrode 200 is at the free end of the nozzle 198. All portions of the flame ionization detector assembly 22, except for heater coil 196 and electrode 200, are made of fused quartz.

Each cooling chamber is connected to a source (not shown) of liquid coolant, such as liquid carbon dioxide. Likewise, the heaters and temperature sensors are connected to respective power supplies and resistance detectors (not shown). The sources of the several gases mentioned also have not been shown, although suitable carrier, purge and makeup gases have been mentioned.

In operation, a sample of material to be analyzed is placed in the cavity 40 and covered by cover 38. The sample tube assembly 12 is then inserted into the annulus of the tubular body 50 and sealed thereagainst by O-ring 51. The first heater assembly 48 is energized to heat the sample and an inert carrier gas, such as helium, is introduced through the port 33 and chamber 32 to form a carrier for the gases generated by pyrolysis of the heated sample. Because the tubular body 50 is formed of quartz and transparent to infrared, the sample is heated rapidly by radiant heat from first heater 48. As the sample evolves volatile materials and/or is heated to a sufficiently high enough temperature to break the sample material down, the gaseous components are swept from chamber 40, by the carrier gas, up through the passage 70 in body 66, to the quartz sand 76 in trap tube 74 where it is trapped as a result of the thermal gradient created by the second cooling chamber 58. After the pyrolysis products have been trapped in quartz sand 76, the first heater 48 is de-energized and first cooling chamber 44 energized to cool chamber 40. The second heater 62 is energized thereby heating and releasing the pyrolysis products from the quartz sand 76 to be swept by the carrier gas into the splitter portion 18. A fraction of the gas passes into the capillary column 102, while the remainder of the gas is purged through the vent 86 by an inert purge gas, such as helium, coming from the purge gas heater coil 120 and sweeping downwardly through the bore of capillary tube 118 to the chamber 84. This back flow of purge gas assures that none of the sample gas and carrier gas contact metal. The sample gas and carrier gas will rise through the helical portion 144 of capillary column 102 where the temperature is again controlled by the third heater 138 and the third cooling chamber 132. The capillary column 102 is coated on its interior with an apolar liquid phase material so that separation of the components of the gases being analyzed occurs. The sample and carrier gases are mixed with a known makeup gas, such as nitrogen, in the upper T-assembly 160 before entering the flame ionization detector assembly 22 where it is mixed with hydrogen from passage 182 and combusted as it exits the nozzle 198 to perform the flame ionization detection function. It will be apparent that other types of detectors such as thermal conductivity detectors, flame photometric detectors, electron capture detectors, or mass spectrometers, etc. can also be used.

The liquid coating material on the interior of capillary column 102 can be any of a myriad of liquid phased materials commonly used in gas-liquid chromatography. Such liquids are generally inert in the sense that they do not chemically react with components passing through the capillary tube, have very high boiling points so as to not "bleed" off of the column and into the detector, and have the ability to affect separation of a multitude of components present in the evolved gases so that the individual components are selectively held on the coating and then released sequentially, normally by gradually increasing the temperature such as by the use of a temperature programmer or the like.

The above process can be repeated at successively higher temperatures in order to analyze all of the sample volatile and breakdown materials.

It should be noted that reference to quartz and fused quartz appear throughout the specification. These terms are intended to include all forms of vitreous silica as well as transparent vitreous silica and the material formed by direct melting of quartz crystals. Preferably, the capillary column 102 is synthetic fused silica, namely a material formed by vapor phase hydrolysis.

It should also be noted that the present invention has been described as an assembly of individual components. In actuality, many of the components, for example those making up splitter assembly 82 and flame ionization detector 22, are fused together with integral units.

The present invention is so constructed that the sample gas will only contact nonreactive materials. The sample gas never comes into contact with a metal.

The pyrolysis apparatus of the present invention makes possible the analysis of complex chemical substances which can be converted into volatile or breakdown materials which, in and of themselves, are reactive and which, in the absence of being subjected to a constantly inert, or non-adsorbent environment such as provided by fused quartz, would recombine or react to form new compounds or be adsorbed thereby providing misleading results as to the chemical makeup of the sample being analyzed.

The foregoing disclosure and description of the invention is illustrative and explanatory thereof, and various changes in the size, shape and materials as well as in the details of the illustrated construction may be made within the scope of the appended claims without departing from the spirit of the invention.

What is claimed is:

1. A pyrolysis apparatus comprising:
   a first, fused quartz tubular member defining an infrared transparent pyrolysis chamber therein, said tubular member defining a gas outlet from said pyrolysis chamber and an inlet to said pyrolysis chamber;
   means for introducing sample material into said pyrolysis chamber formed by said tubular member;
   means for radiantly heating the sample material to effect pyrolysis thereof and to produce gaseous components;
   means for cooling said pyrolysis chamber;
   means for passing a first gas stream through said pyrolysis chamber and out said gas outlet to produce a second gas stream containing gaseous components;
   gas splitter means, said gas splitter means comprising a first quartz tube having an inlet and an outlet, the inlet of said first quartz tube being in open communication with said gas outlet, said gas splitter means further comprising a second quartz tube of smaller diameter than said first quartz tube and having a first end and a second end, the first end of said second quartz tube being received into the outlet of said first quartz tube whereby a smaller fraction of the second gas stream flowing through said first quartz tube is introduced into said first end of said second quartz tube and a larger portion of the second gas stream flowing through said first quartz tube passes through said outlet of said first quartz tube.

2. The apparatus of claim 1 wherein said means for heating the sample material comprises an electrical resistance coil surrounding said first tubular member, said coil being received inside a helical quartz tube in surrounding relationship to said first tubular member.

3. The apparatus of claim 1 wherein said means for introducing sample material comprises:
   a fused quartz sample boat for containing the sample material and received in said pyrolysis chamber; and
   means for introducing the first gas stream into said pyrolysis chamber through said inlet whereby the first gas stream flows around said sample boat.

4. An apparatus according to claim 1 further comprising:
   means defining a chamber around said first quartz tube;
   temperature sensing means in said chamber in close proximity to said first quartz tube; and
   heater means encompassing said chamber and cooling chamber means encompassing said heater means, whereby temperatures within said first quartz tube can be controlled.

5. The apparatus of claim 1 wherein said first quartz tube is at least partially filled with a particulate quartz material.

6. The apparatus of claim 1 wherein said second quartz tube comprises a fused quartz capillary column, said capillary column having a material on an interior thereof to effect separation of gaseous components.

7. The apparatus of claim 6 wherein said capillary column is formed into a helix and further comprising means to control the temperature of said helix.

8. The apparatus of claim 7 wherein said means to control the temperature of said helix comprises:
   an electrical resistance heater surrounding said helix; and
   a cooling chamber enclosing said heater.

9. The apparatus of claim 6 including means defining a mixing chamber, said second end of said capillary column being received in said mixing chamber and means to introduce a third gas stream into said mixing chamber for mixing with the effluent from said capillary column entering said mixing chamber.

10. The apparatus of claim 9 including means for introducing a fourth gas stream into said mixing chamber for mixing with effluent from said capillary column.

11. The apparatus of claim 10 including means for preventing back flow of gas from said mixing chamber into said capillary column.

* * * * *